United States Patent
Cheng et al.

(10) Patent No.: US 11,364,279 B2
(45) Date of Patent: *Jun. 21, 2022

(54) MEDICAMENT USED FOR TREATING HYPERTENSION

(71) Applicant: Shandong Zhonghai Pharmaceutical CO. LTD, Weifang (CN)

(72) Inventors: Long Cheng, Weifang (CN); Baozhen Xu, Weifang (CN); Qian Cheng, Weifang (CN)

(73) Assignee: SHANDONG ZHONGHAI PHARMACEUTICAL CO. LTD, Weifang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/073,876

(22) PCT Filed: Jan. 20, 2017

(86) PCT No.: PCT/CN2017/071813
§ 371 (c)(1),
(2) Date: Jul. 30, 2018

(87) PCT Pub. No.: WO2017/129049
PCT Pub. Date: Aug. 3, 2017

(65) Prior Publication Data
US 2019/0038710 A1    Feb. 7, 2019

(30) Foreign Application Priority Data
Jan. 29, 2016  (CN) .......................... 201610061760.2

(51) Int. Cl.
| | |
|---|---|
| *A61K 38/16* | (2006.01) |
| *A61K 31/4025* | (2006.01) |
| *A61K 35/62* | (2006.01) |
| *A61K 36/02* | (2006.01) |
| *A61K 36/03* | (2006.01) |
| *A61K 36/04* | (2006.01) |
| *A61K 36/05* | (2006.01) |
| *A61K 36/25* | (2006.01) |
| *A61K 36/284* | (2006.01) |
| *A61K 31/7012* | (2006.01) |
| *A61P 9/12* | (2006.01) |
| *A61K 31/715* | (2006.01) |

(52) U.S. Cl.
CPC ........ *A61K 38/168* (2013.01); *A61K 31/4025* (2013.01); *A61K 31/7012* (2013.01); *A61K 31/715* (2013.01); *A61K 35/62* (2013.01); *A61K 36/02* (2013.01); *A61K 36/03* (2013.01); *A61K 36/04* (2013.01); *A61K 36/05* (2013.01); *A61K 36/25* (2013.01); *A61K 36/284* (2013.01); *A61P 9/12* (2018.01)

(58) Field of Classification Search
CPC .. A61K 38/168; A61K 36/05; A61K 31/7012; A61K 36/02; A61K 36/03; A61K 36/04; A61K 36/25; A61K 36/28
See application file for complete search history.

(56) References Cited

U.S. PATENT DOCUMENTS

2013/0101514 A1* 4/2013 Cushing ............... A61K 31/201
424/9.1

FOREIGN PATENT DOCUMENTS

| | | | |
|---|---|---|---|
| CN | 1300623 A | | 6/2001 |
| CN | 101020719 A | | 8/2007 |
| CN | 101352514 A | * | 1/2009 |
| CN | 101461911 A | * | 6/2009 |
| CN | 101703710 A | * | 5/2010 |
| CN | 102077933 A | * | 6/2011 |
| CN | 102417544 A | * | 4/2012 |
| CN | 102824600 A | * | 12/2012 |
| CN | 104435149 A | * | 3/2015 |
| CN | 105597081 A | | 5/2016 |

OTHER PUBLICATIONS

Chiovotti et al. Eur. J. Phycol., 38: 351-360. (Year: 2003).*
Hwang et al. Food and Chemical Toxicology 46 (2008) 3475-3481. (Year: 2008).*
Jung et al. Arch Pharm Res 27(2), 2004, pp. 184-188. (Year: 2004).*
Hikino et al. J Ethnopharmacol. Nov. 1984;12(2):231-5. abstract only. (Year: 1984).*
Lv Kefan et al., Study on Anti-Tumor and Extraction of Natural Glycoproteins, Journal of Harbin University of Commerce ( Natural Sciences Edition), vol. 29 No. 1, Feb. 28, 2013, pp. 1-3.

* cited by examiner

*Primary Examiner* — Amy L Clark
(74) *Attorney, Agent, or Firm* — Bayramoglu Law Offices LLC

(57) ABSTRACT

A medicament for use in treating hypertension. The medicament is a glycoprotein, a mixture of polysaccharide and protein, a polypeptide or a protein.

7 Claims, No Drawings

MEDICAMENT USED FOR TREATING HYPERTENSION

CROSS REFERENCE TO RELATED APPLICATIONS

This application is the national phase entry of International Application No. PCT/CN2017/071813, filed on Jan. 20, 2017, which is based upon and claims priority to Chinese Patent Application No. 201610061760.2, filed on Jan. 29, 2016, the entire contents of which are incorporated herein by reference.

TECHNICAL FIELD

The present invention relates to a medicament for use in treating hypertension and belongs to the field of medical technology.

BACKGROUND

High TC and/or TG or low HDL-C, which is called dyslipidemia in modern medicine, is the common disease and frequently-occurring disease among metabolic diseases in the middle and the old and the main factor for CHD, arteriosclerosis, cerebral thrombus and cerebral hemorrhage. In recent years, hyperlipidemia has young tendency due to high caloric diet and reduction in activity level and threatens people's heath, which has drawn general concern.

There are many kinds of medicaments used to reduce blood fat at present and mainly divided into two categories, traditional Chinese medicine and Western medicine. The side effect of Western medicine is so significant, for example, lipid-lowering agents in statins and fibrates may cause myositis or stroke. There are many kinds of lipid-lowering agents but always has the problem of miscellaneous contents of the medicament, it shall soak, boil, extract, filter, concentrate or add adjuvants during production and the production lacks administration so that the quality is unreliable.

SUMMARY

The present invention provides a medicament for use in treating hypertension in order to solve the deficiencies in the prior art for the purpose to achieve the following objectives hereof:

(1) the medicament hereof reduces the content of triglyceride in serum;
(2) the medicament hereof reduces the content of TC in serum;
(3) the medicament hereof reduces the content of LDL-C in serum;
(4) the medicament hereof increases the content of HDL-C in serum.

In order to solve the above problems, the present invention adopts the following technical solution:

A medicament for use in treating hypertension, is a kind of glycoprotein or the mixture of polysaccharide and protein, or polypeptide, or protein; the glycoprotein comprises 1%-99% of sugar and 1%-99% of protein by weight; the mixture of polysaccharide and protein comprises 1%-99% of polysaccharide and 1%-99% of protein by weight; the glycoprotein has a molecular weight of 0.2-3000 kDa. The following are further modifications to the above technical solution:

wherein the medicament is a marine algal glycoprotein.

The marine algal glycoprotein comprises 1%-99% of sugar and 1%-99% of protein by weight; the mixture of marine algal polysaccharide and protein comprises 1%-99% of sugar and 1%-99% of protein by weight.

The marine algal glycoprotein has a molecular weight of 0.2-3000 kDa;

as for the mixture of polysaccharide and protein, the polysaccharide has a molecular weight of 0.2-3000 kDa and the protein has a molecular weight of 0.2-3000 kDa.

The medicament comprises 1-99 portions of glycoprotein and 1-25 portions of glucuronic acid by weight.

The medicament comprises 1-99 portions of marine algal glycoprotein and 1-27 portions of glucuronic acid by weight.

The medicament comprises 1-99 portions of marine algal glycoprotein, 1-27 portions of glucuronic acid and 2-12 portions of indigo naturalis by weight.

The algae is one kind of the following: blue-green algae, green algae, red algae, gold algae, and brown algae.

The medicament comprises 1-99 portions of marine algal glycoprotein, 5-16 portions of indigo naturalis, and 4-15 portions of *Tetrapanax papyriferus* and 1-14 portions of glucuronic acid by weight.

The medicament comprises 1-99 portions of marine algal glycoprotein, 5-16 of indigo naturalis, 4-15 portions of *Tetrapanax papyriferus*, 7-14 portions of earthworms and 6-11 portions of rhizoma atractylodis by weight.

The medicament comprises 1%-99% of sugar and 1%-99% of protein by weight.

The marine algal glycoprotein comprises 1%-99% of sugar and 1%-99% of protein by weight conten.

Compared with the prior art, the advantages of the present invention are:

(1) the medicament hereof reduces the content of triglyceride in serum, within the 4th week after administration, the content of triglyceride reduces to 1.18-1.37 mmol/L;
(2) the medicament hereof reduces the content of TC in serum, within the 4th week after administration, the content of TC in rats reduces to 2.27-2.56 mmol/L;
(3) the medicament hereof reduces the content of LDL-C in serum, within the 4th week after administration, the content of LDL-C in rats reduces to 4.58-5.26 mmol/L;
(4) the medicament hereof increases the content of HDL-C in serum, within the 4th week after administration, the content of HDL-C in rats reduces to 0.86-0.96 mmol/L.

DETAILED DESCRIPTION OF THE EMBODIMENTS

The preferred embodiments of the present invention are described in the following, and the preferred embodiments described herein are only intended to illustrate and explain the invention, but not limited to this invention.

Embodiment 1

A Medicament for Use in Treating Hypertension

Wherein the medicament is a marine algal glycoprotein;
the marine algal glycoprotein comprises 1% sugar and 99% protein by weight;
the molecular weight is 0.2 kDa;
the sugar is a polysaccharide;
the marine algae is blue-green algae;
the polysaccharide comprises: glucose, galactose, mannose and rhamnose;
the protein comprises: arginine, lysine, serine, and threonine.

Embodiment 2

A Medicament for Use in Treating Hypertension

Wherein the medicament is a marine algal glycoprotein;
the marine algal glycoprotein comprises 7% sugar and 80% protein by weight;
and the molecular weight is 19 kDa;
the marine algae is green algae;
the sugar is a polysaccharide;
the polysaccharide comprises: glucose, galactose, mannose and rhamnose;
the protein comprises: arginine, lysine, serine, and threonine.

Embodiment 3

A Medicament for Use in Treating Hypertension

Wherein the medicament is a marine algal glycoprotein;
the marine algal glycoprotein comprises 15% sugar and 75% protein by weight;
and the molecular weight is 3 kDa;
the marine algae is blue-green algae;
the sugar is a polysaccharide;
the polysaccharide comprises: glucose, galactose, mannose and rhamnose;
the protein comprises: arginine, lysine, serine, and threonine.

Embodiment 4

A Medicament for Use in Treating Hypertension

Wherein the medicament is a marine algal glycoprotein;
the marine algal glycoprotein comprises 30% sugar and 65% protein by weight;
and the molecular weight is 120 kDa;
the marine algae is red algae;
the sugar is a polysaccharide;
the polysaccharide comprises: glucose, galactose, mannose and rhamnose;
the protein comprises: arginine, lysine, serine, and threonine.

Embodiment 5

A Medicament for Use in Treating Hypertension

Wherein the medicament is a marine algal glycoprotein;
the marine algal glycoprotein comprises 51% sugar and 42% protein by weight;
and the molecular weight is 400 kDa;
the marine algae is brown algae;
the sugar is a polysaccharide;
the polysaccharide comprises: glucose, galactose, mannose and rhamnose;
the protein comprises: arginine, lysine, serine, and threonine.

Embodiment 6

A Medicament for Use in Treating Hypertension

Wherein the medicament is a marine algal glycoprotein;
the marine algal glycoprotein comprises 99% sugar and 1% protein by weight;
the molecular weight is 3000 kDa;
the marine algae is gold algae;
the sugar is a polysaccharide;
the polysaccharide comprises: glucose, galactose, mannose and rhamnose;
the protein comprises: arginine, lysine, serine, and threonine;

the glycoprotein in the above embodiments 1-6 further comprises a pigment; the pigment is a natural pigment contained in the algae substance.

The aforementioned embodiments 1-6 are summarized as follows:

A Medicament for Use in Treating Hypertension

The medicament is a glycoprotein;
the glycoprotein comprises 1-99% of sugar and 1-99% of protein by weight;
the molecular weight is 0.2-30000 kDa;
the sugar is a polysaccharide;
the medicament is synthetic glycoproteins and synthetic polysaccharides and proteins.

The protein comprises 20 kinds of amino acids and 8 kinds of synthetic amino acids;

The preparation method of the medicament: the glycoprotein is prepared into capsules and tablets etc. according to routine process; the mixture of polysaccharide and protein is prepared into capsules and tablets etc. according to a conventional process.

Embodiment 7

Application of the Medicament in Treating Hypertension (1) Therapeutic Effect of the Medicament in the Present Invention on Blood Lipids in a Rat Model Experimental animal: SD rats, weighing 160-170 g;

formula of high-fat diet: it is composed of 0.2% of PTU, 2% of cholesterol, 10% of lard, 0.1% of bile salt, 15% of sucrose, 8% of cooked soybean meal, 3% of whole milk powder and basic diet.

Experimental Method:

Rats were randomly divided into 8 groups after entering the laboratory, namely normal control group, model control group, and present invention groups 1-6, 10 rats in each group, weighed and numbered.

Normal control group shall be fed with basic diet, model control group and the groups in this invention shall be fed with high-fat diet, the test period shall be 4 weeks, it shall test contents of triglyceride, TC, HDL-C and LDL-C every week; after 4 weeks, normal control group and model control group shall be given distilled water and 1-6 groups in this invention shall be given the medicament mentioned, the dosage shall be 3 g/d, irrigating for 3 times per day for 3 days successively, testing the contents of triglyceride, TC, HDL-C and LDL-C in serum within the 4th week after administration; the results are shown in Table 1.

TABLE 1

Effect of the medicament hereof on blood lipids in a rat model

| Group | Dose (g/day) | Triglyceride (mmol/L) | Total cholesterol (mmol/L) | HDL (mmol/L) | LDL (mmol/) |
| --- | --- | --- | --- | --- | --- |
| Normal control group | | 0.88 ± 0.17 | 1.68 ± 0.12 | 1.35 ± 0.12 | 0.53 ± 0.13 |
| Model control group | | 2.15 ± 0.19 | 3.92 ± 0.15 | 0.76 ± 0.13 | 6.52 ± 1.7 |
| Embodiment 1 | 3 | 1.37 ± 0.12 | 2.56 ± 0.14 | 0.86 ± 0.12 | 5.23 ± 1.6 |
| Embodiment 2 | 3 | 1.26 ± 0.17 | 2.40 ± 0.11 | 0.87 ± 0.13 | 5.14 ± 1.3 |
| Embodiment 3 | 3 | 1.18 ± 0.14 | 2.27 ± 0.16 | 0.96 ± 0.11 | 4.58 ± 1.4 |
| Embodiment 4 | 3 | 1.25 ± 0.15 | 2.35 ± 0.15 | 0.89 ± 0.10 | 5.07 ± 1.2 |
| Embodiment 5 | 3 | 1.30 ± 0.13 | 2.47 ± 0.21 | 0.90 ± 0.16 | 5.14 ± 1.1 |
| Embodiment 6 | 3 | 1.34 ± 0.21 | 2.54 ± 0.23 | 0.89 ± 0.15 | 5.26 ± 1.5 |

Embodiments 1-6 could reduce the contents of triglyceride, TC and LDL-C effectively and increase the content of HDL-C, the dosage shall be 3 g/d and within the 4th week after administration, the content of triglyceride in rats reduces to 1.18-1.37 mmol/L, the content of TC reduces to 2.27-2.56 mmol/L, the content of LDL-C 4.58-5.26 mmol/L and the content of HDL-C increases to 0.86-0.96 mmol/L, Embodiment 3 is the preferred Embodiment.

Embodiment 8

A Medicament for Use in Treating Hypertension

It comprises 1 portion of marine algal glycoprotein and 1 portion of glucuronic acid by weight.

The marine algal glycoprotein comprises 8% sugar and 82% protein by weight;

the molecular weight is 8 kDa;

the marine algae is blue-green algae;

the sugar is a polysaccharide;

the polysaccharide comprises: glucose, galactose, mannose and rhamnose;

the protein comprises: arginine, lysine, serine, and threonine.

Embodiment 9

A Medicament for Use in Treating Hypertension

Like Embodiment 8, only the ratio of marine algal glycoprotein to glucuronic acid is changed as follows:

It comprises 34 portions of marine algal glycoprotein and 9 portions of glucuronic acid by weight.

Embodiment 10

A Medicament for Use in Treating Hypertension

Like Embodiment 8, only the ratio of marine algal glycoprotein to glucuronic acid is changed as follows:

It comprises 63 portions of marine algal glycoprotein and 19 portions of glucuronic acid by weight.

Embodiment 11

A Medicament for Use in Treating Hypertension

Like Embodiment 8, only the ratio of marine algal glycoprotein to glucuronic acid is changed as follows:

It comprises 99 portions of marine algal glycoprotein and 27 portions of glucuronic acid by weight.

Embodiment 12

A Medicament for Use in Treating Hypertension

It comprises 1 portion of marine algal glycoprotein, 1 portion of glucuronic acid and 2 portions of indigo naturalis by weight.

The marine algal glycoprotein comprises 18% sugar and 75% protein by weight;

and the molecular weight is 20 kDa;

the marine algae is blue-green algae;

the sugar is a polysaccharide;

the polysaccharide comprises: glucose, galactose, mannose and rhamnose;

the protein comprises: arginine, lysine, serine, and threonine.

Embodiment 13

A Medicament for Use in Treating Hypertension

Like Embodiment 12, only the weight ratio of marine algal glycoprotein, glucuronic acid and indigo naturalis is changed as follows:

It comprises 27 portions of marine algal glycoprotein, 7 portions of glucuronic acid and 5 portions of indigo naturalis by weight.

Embodiment 14

A Medicament for Use in Treating Hypertension

Like Embodiment 12, only the weight ratio of marine algal glycoprotein, glucuronic acid and indigo naturalis is changed as follows:

It comprises 56 portions of marine algal glycoprotein, 16 portions of glucuronic acid and 9 portions of indigo naturalis by weight.

Embodiment 15

A Medicament for Use in Treating Hypertension

Like Embodiment 12, only the weight ratio of marine algal glycoprotein, glucuronic acid and indigo naturalis is changed as follows:

It comprises 99 portions of marine algal glycoprotein, 27 portions of glucuronic acid and 12 portions of indigo naturalis by weight.

Application of the Medicament Mentioned in the above Embodiment 8-Embodiment 15 in Reduction of Hypertension Using the test method in Embodiment 7, the medicaments in Embodiment 8-Embodiment 15 in this invention group have the following application effects:

TABLE 2

Effect of the medicament hereof on blood lipids in a rat model

| Group | Dose (g/day) | Triglyceride (mmol/L) | Total cholesterol (mmol/L) | HDL (mmol/L) | LDL (mmol/) |
|---|---|---|---|---|---|
| Normal control group | | 0.88 ± 0.17 | 1.68 ± 0.12 | 1.35 ± 0.12 | 0.53 ± 0.13 |
| Model control group | | 2.15 ± 0.19 | 3.92 ± 0.15 | 0.76 ± 0.13 | 6.52 ± 1.7 |
| Embodiment 8 | 3 | 1.17 ± 0.12 | 2.26 ± 0.14 | 0.91 ± 0.16 | 4.73 ± 1.6 |
| Embodiment 9 | 3 | 0.90 ± 0.18 | 1.86 ± 0.11 | 1.2 ± 0.17 | 2.24 ± 1.3 |
| Embodiment 10 | 3 | 1.18 ± 0.16 | 2.27 ± 0.16 | 0.90 ± 0.15 | 4.88 ± 1.4 |
| Embodiment 11 | 3 | 1.19 ± 0.12 | 2.25 ± 0.15 | 0.89 ± 0.13 | 5.00 ± 1.2 |
| Embodiment 12 | 3 | 1.20 ± 0.13 | 2.29 ± 0.21 | 0.92 ± 0.16 | 4.84 ± 1.1 |
| Embodiment 13 | 3 | 0.93 ± 0.21 | 1.84 ± 0.23 | 1.23 ± 0.15 | 2.36 ± 1.5 |
| Embodiment 14 | 3 | 1.22 ± 0.22 | 2.30 ± 0.20 | 0.92 ± 0.10 | 4.72 ± 1.3 |
| Embodiment 15 | 3 | 1.23 ± 0.18 | 2.24 ± 0.19 | 0.93 ± 0.15 | 4.69 ± 1.5 |

In Embodiments 8-11, an experiment was performed with a changed ratio of marine algal glycoprotein and glucuronic acid, and it turned out, Embodiment 9 was a preferred embodiment. In Embodiment 12-Embodiment 15, by changing the ratio of marine algal glycoprotein, glucuronic acid and indigo naturalis, the experiment found that, Embodiment 13 was a preferred embodiment.

Embodiment 16

A Medicament for Use in Treating Hypertension

It comprises 1 portion of marine algal glycoprotein, 5 portions of indigo naturalis, 4 portions of ammonium cardamomum, and 1 portion of glucuronic acid by weight.

The marine algal glycoprotein comprises 25% sugar and 70% protein by weight;
  the molecular weight is 200 kDa;
  the marine algae is blue-green algae;
  the sugar is a polysaccharide;
  the polysaccharide comprises: glucose, galactose, mannose and rhamnose;
  the protein comprises: arginine, lysine, serine, and threonine.

Embodiment 17

A Medicament for Use in Treating Hypertension

It comprises 47 portions of marine algal glycoprotein, 13 portions of indigo naturalis, 7 portions of *Tetrapanax papyriferus*, and 6 portions of glucuronic acid by weight.

The marine algal glycoprotein comprises 25% sugar and 70% protein by weight;
  and the molecular weight is 3000 kDa;
  the marine algae is blue-green algae;
  the sugar is a polysaccharide;
  the polysaccharide comprises: glucose, galactose, mannose and rhamnose;
  the protein comprises: arginine, lysine, serine, and threonine.

Embodiment 18

A Medicament for Use in Treating Hypertension

It comprises 99 portions of marine algal glycoprotein, 16 portions of indigo naturalis, 15 portions of *Tetrapanax papyriferus*, and 14 portions of glucuronic acid by weight.

The marine algal glycoprotein comprises 25% sugar and 70% protein by weight;
  and the molecular weight is 20 kDa;
  the marine algae is Bangiaatropurpurea (Roth) *C. Agardh*;
  the sugar is a polysaccharide;
  the polysaccharide comprises: glucose, galactose, mannose and rhamnose;
  the protein comprises: arginine, lysine, serine, and threonine.

Embodiment 19

A Medicament for Use in Treating Hypertension

The medicament, comprises 1 portion of marine algal glycoprotein, 5 portions of indigo naturalis, 4 portions of *Tetrapanax papyriferus*, 7 portions of earthworms and 6 portions of rhizoma atractylodis by weight.

The marine algal glycoprotein 45% comprisessugar and 50% protein by weight;
  the molecular weight is 6 kDa;
  the marine algae is gulfweed;
  the sugar is a polysaccharide;
  the polysaccharide comprises: glucose, galactose, mannose and rhamnose;
  the protein comprises: arginine, lysine, serine, and threonine.

Embodiment 20

A Medicament for Use in Treating Hypertension

The medicament, comprises 54 portions of marine algal glycoprotein, 14 portions of indigo naturalis, 12 portions of *Tetrapanax papyriferus*, 11 portions of earthworms and 9 portions of rhizoma atractylodis by weight.

The marine algal glycoprotein comprises 45% sugar and 50% protein by weight;
  and the molecular weight is 12 kDa;
  the marine algae is gulfweed;
  the sugar is a polysaccharide;
  the polysaccharide comprises: glucose, galactose, mannose and rhamnose;
  the protein comprises: arginine, lysine, serine, and threonine.

Embodiment 21

A Medicament for Use in Treating Hypertension

The medicament, comprises 99 portions of marine algal glycoprotein, 16 portions of indigo naturalis, 15 portions of *Tetrapanax papyriferus*, 14 portions of earthworms and 11 portions of rhizoma atractylodis by weight.

The marine algal glycoprotein comprises 45% sugar and 50% protein by weight;

and the molecular weight is 200 kDa;

the marine algae is gulfweed;

the sugar is a polysaccharide;

the polysaccharide comprises: glucose, galactose, mannose and rhamnose;

the protein comprises: arginine, lysine, serine, and threonine.

Application of the Medicament mentioned in the above Embodiments 16-21 for Treating Hypertension Using the test method mentioned in Embodiment 7 and the medicament mentioned in Embodiments 16-21 in this invention groups have the following application effects:

TABLE 3

Effect of the medicament hereof on blood lipids in a rat model

| Group | Dose (g/day) | Triglyceride (mmol/L) | Total cholesterol (mmol/L) | HDL (mmol/L) | LDL (mmol/) |
|---|---|---|---|---|---|
| Normal control group | | 0.88 ± 0.17 | 1.68 ± 0.12 | 1.35 ± 0.12 | 0.53 ± 0.13 |
| Model control group | | 2.15 ± 0.19 | 3.92 ± 0.15 | 0.76 ± 0.13 | 6.52 ± 1.7 |
| Embodiment 16 | 3 | 1.07 ± 0.13 | 2.12 ± 0.14 | 1.12 ± 0.16 | 3.53 ± 1.5 |
| Embodiment 17 | 3 | 0.68 ± 0.14 | 1.52 ± 0.13 | 1.40 ± 0.12 | 1.24 ± 1.3 |
| Embodiment 18 | 3 | 1.08 ± 0.15 | 2.07 ± 0.12 | 1.18 ± 0.13 | 3.68 ± 1.4 |
| Embodiment 19 | 3 | 1.09 ± 0.13 | 2.05 ± 0.14 | 1.06 ± 0.11 | 3.45 ± 1.2 |
| Embodiment 20 | 3 | 0.65 ± 0.12 | 1.49 ± 0.19 | 1.42 ± 0.14 | 1.35 ± 1.1 |
| Embodiment 21 | 3 | 0.97 ± 0.20 | 1.99 ± 0.13 | 1.13 ± 0.15 | 3.06 ± 1.3 |

In Embodiments 16-18, only the weight ratio of the marine algal glycoprotein, indigo naturalis, *Tetrapanax papyriferus* and glucuronic acid is changed. From the experimental results, Embodiment 17 is the most preferred embodiment.

In Embodiments 19-21, only the weight ratio of the marine algal glycoprotein, indigo naturalis, *Tetrapanax papyriferus*, earthworms and rhizoma atractylodis is changed. From the experimental results, Embodiment 20 is the most preferred embodiment.

Embodiment 22

A Medicament for Use in Treating Hypertension

It comprises the following components by weight:

70 portions of glycoprotein in marine algae, 5 portions of Gansui, 10 portions of Chinese lobelias, 7 portions of Eucommia, 6 portions of *Myristica fragrans*, 3 portions of buck grasses and 2 portions of plantain seeds.

The glycoprotein is a marine algal glycoprotein;

the marine algal glycoprotein comprises 7% sugar and 80% protein by weight;

the molecular weight is 8 kDa;

the marine algae is blue-green algae.

Using the test method mentioned in Embodiment 7 and the medicament mentioned in Embodiment 22 in this invention groups have the following application effects:

TABLE 4

Effect of the medicament hereof on blood lipids in a rat model

| Group | Dose (g/day) | Triglyceride (mmol/L) | Total cholesterol (mmol/L) | HDL (mmol/L) | LDL (mmol/) |
|---|---|---|---|---|---|
| Normal control group | | 0.88 ± 0.17 | 1.68 ± 0.12 | 1.35 ± 0.12 | 0.53 ± 0.13 |
| Model control group | | 2.15 ± 0.19 | 3.92 ± 0.15 | 0.76 ± 0.13 | 6.52 ± 1.7 |
| Embodiment 22 | 3 | 0.75 ± 0.14 | 1.70 ± 0.13 | 1.30 ± 0.12 | 1.24 ± 1.3 |

Embodiment 23

The Effect of the Medicament in the Invention on Reduction of Hypertension and Breakdown of Thrombus Clinical trials were carried on the medicaments in Embodiments 8-22 hereof at the dose of three times per day, 1 g per time and the results are shown in Table 5 and Table 6.

TABLE 5

| | | Whole blood viscosity | Fibrin mg % | AT-III % | Plasmiongen U | Prothrombin time (time s) |
|---|---|---|---|---|---|---|
| Before administration | | 5.28 | 479.12 | 104.5 | 6.99 | 12.15 |
| After administration | Embodiment 8 | 4.56 | 435.6 | 80.56 | 7.25 | 12.59 |
| | Embodiment 9 | 3.58 | 300.56 | 48.25 | 7.89 | 14.58 |
| | Embodiment 10 | 4.52 | 430.5 | 82.4 | 7.28 | 12.65 |
| | Embodiment 11 | 4.41 | 428.9 | 80.9 | 7.31 | 12.75 |
| | Embodiment 12 | 4.30 | 425.7 | 79.8 | 7.33 | 12.79 |
| | Embodiment 13 | 3.42 | 295.26 | 46.53 | 7.97 | 14.86 |
| | Embodiment 14 | 4.36 | 400.25 | 78.5 | 7.41 | 12.87 |
| | Embodiment 15 | 4.25 | 412.4 | 77.5 | 7.46 | 12.89 |

TABLE 6

| | | Whole blood viscosity | Fibrin mg % | AT-III % | Plasmiongen U | Prothrombin time (time s) |
|---|---|---|---|---|---|---|
| Before administration | | 5.28 | 479.12 | 104.5 | 6.99 | 12.15 |
| After administration | Embodiment 16 | 4.46 | 430.6 | 80.36 | 7.28 | 12.69 |
| | Embodiment 17 | 3.50 | 300.16 | 46.25 | 7.99 | 14.88 |
| | Embodiment 18 | 4.50 | 432.5 | 81.4 | 7.30 | 12.61 |
| | Embodiment 19 | 4.35 | 427.9 | 80.4 | 7.35 | 12.78 |
| | Embodiment 20 | 3.45 | 294.26 | 45.23 | 7.99 | 14.96 |
| | Embodiment 21 | 4.2 | 426.5 | 78.8 | 7.36 | 12.63 |
| | Embodiment 22 | 3.42 | 290.4 | 42.6 | 8.07 | 15.20 |

Embodiment 24

A Preparation Method of the Medicament for Use in Treating Hypertension

Step 1: Weighing weighing the marine algal glycoprotein and all Chinese medicine components according to the formula.

Step 2: Extraction of Chinese Medicine (1) Washing

Washing all Chinese medicine components with clear water, and remove the impurities;

(2) Crashing and Microwave Extraction the Chinese medicine is pulverized into 100-mesh medicinal material powder, 10 times of 50% ethanol is added, the temperature is controlled at 60° C., microwave radiation is performed at the microwave irradiation of 260 W, microwave wavelength of 130 mm, a frequency of 1200 MHz for 5 min, then filtration is carried out, and finally the filtrate is collected;

the medicine dregs are separated, 12 times of clear water is added, the temperature is controlled at 50° C., microwave radiation is performed at the microwave irradiation of 200W, microwave wavelength of 1430 mm, a frequency of 1250 MHz for 5 min, then filtration is carried out, and finally the filtrate is collected;

combining the filtrate in two times and conducting spray drying to prepare Chinese traditional medicinal powder;

for the spray drying mentioned, filtering the filtrate in traditional Chinese medicine in combination for two times through the filterable membrane in 0.45 μm of micropore to obtain the filtrate, and then the filtrate obtained shall be led in bi-directional SPJT of small spray drier in type Büchi290, the control temperature at inlet is 125° C., the feeding speed is 3 mL/min to conduct spray drying.

Step 3: Adding Marine Algal Glycoprotein

Mixing the powder of glycoprotein in marine algae with the above powder of traditional Chinese medicine to produce different dosage forms such as capsules and tablets;

for the medicament mentioned in the invention, pH is between 5.3-9.8 and 6.5-7.5 is preferred;

the present invention has been subjected to a large number of experiments, and we have carried out multiple tests using a mixture of marine shells, bones of livestock and poultry, a mixture of glycoprotein, polysaccharides and proteins extracted from the skeleton of marine animals, and the objectives of the invention have also been achieved.

Embodiment 25

A Medicament for Use in Treating Hypertension

The medicament is a mixture of polysaccharides and proteins;

the medicament comprises 1-99% of polysaccharide and 1-99% of protein by weight;

the polysaccharide comprises: glucose, galactose, mannose and rhamnose;

the protein mentioned comprises: Asparagine, cysteine, lysine, arginine, serine, threonine, alanine, aspartic acid, glutamine, glutamic acid, histidine, isoleucine, glycine Leucine, methionine, phenylalanine, valine, tyrosine, and valine.

As for the mixture of polysaccharide and the protein, the polysaccharide has a molecular weight of 0.2-3000 kDa and the protein has a molecular weight of 0.2-3000 kDa.

The mixture of polysaccharides and proteins, further a mixture of algal polysaccharides and algal proteins;

a mixture of the algal polysaccharide and the algal protein also comprises a pigment;

the pigment is a natural pigment contained in the algal substance;

the algal protein may be phycocyanin, phycoerythrin or algae xanthoprotein.

The glycoprotein comprises synthetic glycoprotein, synthetic polysaccharide and protein.

The medicament hereof has a No Observed Adverse Effect Level (NOAEL) of 1.6 g/kg for 12-week oral administration for dogs, which is equivalent to 50 times the equivalent dose for humans, so it is concluded that the safety of the clinical trial can be guaranteed.

The medicine described in the invention can also be a health care product or a food.

The basic principles and main features of the present invention and the advantages of the present invention are shown and described above. It should be understood by the technicians in this field that, the present invention is not limited by the foregoing embodiments, and that what are described in the aforementioned embodiments and instructions are only the principles of this invention; without departing from the spirit and scope of the invention, this invention may be subject to various changes and modifications, which will be included within the scope of the invention as claimed. The scope of the invention is defined by the appended claims and their equivalents.

What is claimed is:

1. A medicament for treating hypertension,
   wherein the medicament causes at least one of an increase in HDL-C serum content and a reduction in at least one of triglyceride serum content, TC serum content and LDL-C serum content, comprising:
   an amount of marine algal glycoprotein and an amount of glucuronic acid selected from the group consisting of 1 portion of marine algal glycoprotein and 1 portion of glucuronic acid by weight, 34 portions of marine algal glycoprotein and 9 portions of glucuronic acid by weight, 63 portions of marine algal glycoprotein and 19 portions of glucuronic acid by weight, and 99 portions of marine algal glycoprotein and 27 portions of glucuronic acid by weight,
   wherein the marine algal glycoprotein is obtained from marine algae,
   the marine algae are one or more selected from the group consisting of blue-green algae, green algae, red algae, gold algae and brown algae,
   the medicament is in a form of a capsule or a tablet, and
   the medicament is configured to treat the hypertension.

2. The medicament according to claim 1, wherein the marine algal glycoprotein comprises 1%-99% of sugar and 1%-99% of protein by weight.

3. The medicament according to claim 1, wherein the marine algal glycoprotein molecular weight is 0.2-3000 kDa.

4. The medicament according to claim 1, wherein the medicament further comprises 2-12 portions of indigo naturalis by weight.

5. The medicament according to claim 1, wherein the medicament further comprises 5-16 portions of indigo naturalis, and 4-15 portions of Tetrapanax papyriferus by weight.

6. The medicament according to claim 1, wherein the medicament further comprises 5-16 portions of indigo naturalis, 4-15 portions of Tetrapanax papyriferus, 7-14 portions of earthworms and 6-11 portions of rhizoma atractylodis by weight.

7. The medicament according to claim 1, wherein the medicament further comprises 13-14 portions of indigo naturalis by weight.

* * * * *